United States Patent [19]

Klipstein et al.

[11] 4,411,888
[45] Oct. 25, 1983

[54] COMPOSITION OF A NOVEL IMMUNOGEN FOR PROTECTION AGAINST DIARRHEAL DISEASE CAUSED BY ENTEROTOXIGENIC *ESCHERICHIA COLI*

[75] Inventors: Frederick A. Klipstein, Rochester; Richard E. Engert, Webster; John D. Clements, Pittsford, all of N.Y.

[73] Assignee: The University of Rochester, Rochester, N.Y.

[21] Appl. No.: 403,751
[22] PCT Filed: Jun. 3, 1982
[86] PCT No.: PCT/US82/00763
§ 371 Date: Jun. 3, 1982
§ 102(e) Date: Jun. 3, 1982
[87] PCT Pub. No.: WO83/00018
PCT Pub. Date: Jan. 6, 1983

Related U.S. Application Data

[63] Continuation-in-part of Ser. No. 276,409, Jun. 22, 1981, abandoned.

[51] Int. Cl.³ ............... A61K 39/108; A61K 39/106
[52] U.S. Cl. .................................. 424/92; 424/88
[58] Field of Search ........................... 424/88, 92

[56] References Cited

U.S. PATENT DOCUMENTS 4,220,584  9/1980  Limyuco et al. ............... 424/92
4,314,993  2/1982  Weynendaele ................. 424/92

OTHER PUBLICATIONS

Deneke, R. et al., Infect. Immun., vol. 32, pp. 1254–1260, 1981.
Gill, D. M. et al., Infect. Immun., vol. 33, pp. 677–682, 1981.
Holmgren, J., Nature, vol. 292, pp. 413–417, 1981.
Clements, J. D., et al., Infect. Immun., vol. 22, pp. 709–713, 1981.
Pierce, N. F., Infect. Immun., vol. 18, pp. 338–341, 1977.
Klipstein, F. A., et al., Infect. Immun., vol. 31, pp. 144–150, 1981.
Klipstein, F. A., et al., Infect. Immun., vol. 32, pp. 1100–1104, 1981.
Frantz, J. C., et al., Infect. Immun., vol. 33, pp. 193–198, 1981.
Giannella, R. A., et al., Infect. Immun., vol. 33, pp. 186–192, 1981.
Klipstein, F. A., et al., Infect. Immun., vol. 34, pp. 637–639, 1981.
Klipstein, F. A., et al., Infect. Immun., vol. 23, pp. 592–599, 1979.
Clements, J. D., et al., Infect. Immun., vol. 24, pp. 760–769, 1979.
Staples, S. J., et al., J. Biol. Chem., vol. 255, pp. 4716–4721, 1980.
Chan, S., et al., J. Biol. Chem., vol. 256, pp. 7744–7746.
Klipstein et al., J. Infect. Dis., vol. 147, No. 2, pp. 318–325, 1983.
Erlanger, B., Pharmacological Reviews, vol. 25, pp. 271–280, 1973.
Peters et al., Ann. Rev. Biochem., vol. 46, pp. 523–551, 1977.

*Primary Examiner*—Blondel Hazel
*Attorney, Agent, or Firm*—Martin LuKacher

[57] ABSTRACT

There is disclosed a novel immunogen which can be used for immunological protection against acute diarrheal disease caused by enterotoxigenic strains of *Escherichia coli*. The novel immunogen is provided by cross-linking the *E. coli* heat-stable enterotoxin with the *E. coli* heat-labile enterotoxin (either the complete holotoxin or just the B subunit of this toxin) by a conjugation process in the presence of a conjugating agent, typically the water soluble carbodiimide, 1-ethyl-3-(3-diamethylaminopropyl) carbodiimide. This results in a unique new molecule in that the toxic properties of each individual toxin are greatly reduced, the heat-labile toxin (or its B subunit) retains its antigenicity, and the heat-stable toxin acquires immunogenicity as a function of the reaction. Immunization with the cross-linked immunogen provides immunological protection in mammals against water secretion induced by strains of *E. coli* which produce the heat-labile or heat-stable enterotoxins, either singly or together.

18 Claims, 5 Drawing Figures

COMPOSITION OF A NOVEL IMMUNOGEN FOR PROTECTION AGAINST DIARRHEAL DISEASE CAUSED BY ENTEROTOXIGENIC ESCHERICHIA COLI

BACKGROUND

This application is a continuation in part of application Ser. No. 06/276,409, filed June 22, 1981, now abandoned.

Acute diarrheal disease due to transient colonization of the small intestine by enterotoxigenic strains of *Escherichia coli* (ETEC) is a major health problem of global scope. These organisms and rotavirus are the two principal causes of acute diarrhea in young children, which, according to World Health Organization estimates, accounts for approximately ten million deaths per annum among infants, mostly in those living in underdeveloped tropical countries (See Black, R. E., et al. 1981. Incidence and severity of rotavirus and *Escherichia coli* diarrhea in rural Bangladesh. Lancet 1:141–143). Enterotoxigenic *E. coli* are also the principal cause of acute diarrhea among persons from temperate zones who travel to the tropics (turista), a common cause of sporadic episodes of diarrhea among adults living in temperate and tropical areas, and a major problem in animal husbandry by virtue of their causing frequently fatal acute diarrhea among weanling animals, especially in lambs and piglets.

The mechanisms by which ETEC strains cause diarrhea have been elucidated. Following peroral ingestion, the bacteria adhere to the surface of the intestinal mucosa of the proximal small bowel; this process is enhanced by the presence on the surface of the bacteria of plasmid-induced specific fimbrial antigens which are host specific and are referred to as colonization factors in human strains (See, Evans, D. G., et al. 1978. New surface-associated heat-labile colonization factor antigen (CFA/II) produced by enterotoxigenic *Escherichia coli* of serogroups 06 and 08. Infect. Immun. 21:638–647). There appear to be multiple, antigenically dissimilar fimbrial antigens in human ETEC strains, and no specific fimbrial antigen has been detected in the case of some pathogenic ETEC strains (See Deuke, R. et al. 1981. Serotypes of attachment pili of enterotoxigenic *Escherichia coli* isolated from humans. Infect. Immunm. 32:1254–1260 and Levine, M. M., et al. 1980. Hemagglutination and colonization factors in enterotoxigenic and enteropathogenic *Escherichia coil* that cause diarrhea J. Infec. Dis. 141:733–737. The bacteria proliferate in this location and elaborate two plasmid-induced enterotoxins, either singly or together: a heat-labile (LT) toxin and a heat-stable (ST) toxin.

The holotoxin (complete toxin) of the LT toxin has recently been isolated in purified form and characterized (See, Clements, J. D., et al. 1979. Isolation and characterization of homogeneous heat-labile enterotoxins with high specific activity from *Escherichia coli* cultures. Infect. Immun. 24:760–769). It consists of five B subunits (MW 12,000 daltons each) and one A subunit (MW 31,500 daltons) as reported by Gill, D. M. et al. 1981. Subunit number and arrangement of *Escherichia coli* heat-labile enterotoxin. Infec. Immun. 33:677–682. The B subunits are responsible for attaching the toxin to specific $GM_1$ ganglioside receptors on the surface of the intestinal mucosa, thereby permitting penetration of the cell by the A subunit which stimulates intracellular adenylate cyclase which is responsible for secretion of fluid and electrolytes ito the intestinal lumen. It is noteworthy that the *E. coli* LT toxin functionally, structurally and immunologically resembles the toxin produced by *Vibrio cholerae* (cholera toxin). Both LT and cholera toxin (CT) consist of the same type and number of subunits which have approximately the same molecular weight; the subunits serve the same functions, and the LT and CT have shared and distinct antigenic determinants in both of their A and B subunits (See Holmgren, J., 1981. Actions of cholera toxin and the prevention and treatment of cholera. Nature 292:413–417 and Clements, J. D. et al. 1978. Shared and unique immunological determinants of enterotoxins from *Vibrio cholerae* and *Escherichia coli*. Infec. Immun. 22:709–713). Further, immunization of rats with LT or cholera toxin provides protection against challenge with the LT toxin (See, Pierce, N. F. 1977. Protection against challenge with *Escherichia coli* heat-labile enterotoxin by immunization of rats with cholera toxin-toxoid. Infect. Immun. 18:338–341. and Klipstein, F. A. et al. 1981. Protective effect of immunization of rats with holotoxin or B subunit of *Escherichia coli* heat-labile enterotoxin. Infect. Immun. 31:144–150).

*E. coli* heat-stable toxin (ST) obtained from a human strain has recently been characterized in purified form, as reported in Staples, S. J., et al., 1980. Purification and characterization of heat-stable enterotoxin produced by a strain of *E. coli* pathogenic for man. J. Biol. Chem. 255:4716–4721. ST has a molecular weight of approximately 2,000 daltons. It is uncertain how this toxin attaches to the surface of the mucosal cell; once located intracellularly, it causes fluid and electrolyte secretion by means of stimulating intracellular guanylate cyclase. Approximately 20% of human ETEC strains produce just LT (LT+/ST−), 60% produce both LT and LT (LT+/ST+) and 20% elaborate only ST (LT−/ST+); each of these types is capable of causing acute diarrhea.

The most practical approach for the prevention of the widespread morbidity and mortality caused by diarrheal disease due to intestinal contamination with ETEC strains of *E. coli* would be by means of a program of protective vaccination. Three different types of *E. coli* antigen have been shown to be effective as immunogens which provide protection against challenge with ETEC strains in experimental models.

(i) Immunization with somatic antigens (usually in the form of the killed whole bacterim) prevents diarrhea by means of reducing bacterial growth within the small intestine; this, however, extends only to homologous somatic serotypes and not to heterologous serotypes of which 164 antigenically dissimilar somatic serotypes of *E. coli* are recognized (See, Gay, C. C., 1971. Problems of immunization in the control of *Escherichia coli* infection. Ann. N.Y. Acad. Sci. 176:336–349).

(ii) Immunization with the specific fimbrial antigen responsible for adherence and colonization of the bacteria on the surface of the intestinal mucosa also provides protection, but this does not extend to ETEC strains possessing antigenically different fimbrial antigens (See, Morgan, R. L., et al., 1978. Immunization of suckling pigs against enterotoxigenic *Escherichia coli*-induced diarrheal disease by vaccinating dams with purified 987P or K99pili: Protection correlates with pilus homology of vaccine and challenge. Infect. Immun. 22:771–777) and multiple antigenically dissimilar fimbrial antigens have been detected among animal and human ETEC strains (as cited above).

(iii) Immunization with either the *E. coli* LT holotoxin or its B subunit arouses an antitoxin response which provides protection against active challenge with the toxin itself and viable bacterial strains which produce just LT (LT+/ST−) as well as LT and ST toxins (LT+/ST+) (See, Klipstein F. A. et al., 1979. Protective effect of active immunization with purified *Escherichia coli* heat-labile enterotoxin in rats. Infect. Immun. 23:592–599 and Klipstein, F. A. et al. 1981. Protective effect of immunization of rats with the holotoxin of B subunit of *Escherichia coli* heat-labile enterotoxin. Infect. Immun. 31:144–150). LT produced by different somatic serotypes is antigenically homogeneous and thus immunization with this toxin provides protection against all LT-producing strains irrespective of their somatic serotypes or fimbrial antigens (See, Klipstein, F. A., et al. 1981. Immunication of rats with heat-labile enterotoxin provides uniform protection against heterologous serotypes of enterotoxigenic *Escherichia coli* Infect. Immun. 32:1100–1104). Immunization with LT or its B subunit does not, however, provide protection against ETEC strains which produce just the ST toxin (LT−/ST+) (See, Klipstein, F. A., et al., 1979. Cited above).

The low molecular weight ST toxin is nonantigenic; recently, however, procedures have been described for obtaining purified ST from bovine, porcine and human ETEC strains and several studies have shown that ST is haptenic. Immunization of rabbits or goats with purified ST coupled to a large molecular weight carrier, such as bovine serum albumin or bovine immunoglobulin G, has been shown to arouse antitoxin to ST, as demonstrated by the ability of the antiserum to neutralize the activity of ST in the suckling mouse assay (See, Frantz, J. C., et al., 1981. Immunological properties of *Escherichia coli* heat-stable enterotoxins: development of a radioimmunoassay specific for heat-stable enterotoxins with suckling mouse activity. Infect. Immun. 33:193–198, and Giannella, R. A., et al., 1981. Development of a radioimmunoassay for *Escherichia coli* heat-stable enterotoxin: comparison with the suckling mouse bioassay. Infect. Immun. 33:186–192). Further, immunization of rats with a semipurified preparation of ST coupled to porcine immunoglobulin has been shown to provide protection against active challenge with either the ST toxin or viable strains which produce just this toxin, but not against the LT toxin or LT-producing viable strains (See, Klipstein, F. A., et al. 1982. Protection in rats immunized with *Escherichia coli* heat-stable enterotoxin. Infec. Immun. 34:637–639).

None of these toxin forms are acceptable for use as a vaccine for immunization against ETEC strains of *E. coli*. The LT holotoxin itself (or cholera toxin) is not a practical immunogen for use in human immunization for several reasons. Firstly, its immunogenic form retains toxicity which would result in unacceptable side reactions (muscle and skin inflammation when given parenterally and diarrhea when given perorally) if administered to humans. Secondly, immunization with either the LT holotoxin or its B subunit provides no protection against those ETEC strains that produce just the ST toxin (See, Klipstein, F. A., et al. 1979. Protective effect of active immunization with purified *Escherichia coli* heat-labile enterotoxins in rats. Infect. Immun. 23:592–599), which are also a common cause of acute diarrhea. The ST toxin is not practical since it is toxic; it is nonantigenic and the large molecular weight carriers of animal protein needed to render it immunogenic are unsafe for human use; and immunization with this toxin fails to provide protection against ETEC strains which produce the LT toxin.

Thus, what is needed is a vaccine composed of a novel immunogen (a) that would provide immunological protection against ETEC strains which produce either LT or ST, (b) in which the ST toxin is rendered immunogenic, (c) whose toxicity is sufficiently attenuated so that immunization with this material does not yield adverse side reactions, and (d) which contains the B subunit (either alone or as part of the LT holotoxin) that would enhance peroral immunization by virtue of its property of attaching to specific receptor sites on the surface of the intestinal mucosa, thus permitting prolonged exposure of the mucosal cells to the immunogen.

SUMMARY OF THE INVENTION

It is, therefore, an object of this invention to provide a novel composition that is nontoxic but effective in providing immunological protection in mammals against acute diarrheal disease caused by enterotoxigenic strains of *E. coli* which produce LT or ST, either singly or together.

Another object of this invention is to provide a novel vaccine for the prevention of ETEC induced acute diarrheal disease.

Another object of this invention is to provide a vaccine which provides protection against ETEC organisms which produce either LT or ST.

Another object of this invention is to provide a composition combining ST and LT (or its B subunit) wherein the toxic properties of the individual toxins are reduced, their respective antigenicity is retained, and the property of the B subunit to adhere to specific mucosal receptors is maintained.

In accordance with this invention there is provided the product of the process of reacting the heat-labile (LT) enterotoxin (either in the form of the holotoxin or just its B subunit) or cholera toxin (either in the form of the holotoxin or just its B subunit) and heat-stable (ST) enterotoxin of *Escherichia coli* in the presence of a suitable conjugating reagent. While not being held to any single theory, it is proposed that the product of the above described process is a cross-linked molecule via the available carboxyl and amino groups in each of the LT or CT and ST molecules and, additionally, involving intrachain linking of the LT or CT molecule. Accordingly, as employed in this specification and claims, the product of the process of reacting ST with a reactant selected from the group consisting of LT or CT holotoxin is referred to as cross-linked ST-LT or ST-CT and that of reacting ST to the B subunit as cross-linked ST-B.

The above cross-linked molecules are effective in a vaccination method wherein the composition is administered together with a suitable adjuvant for both primary immunization and booster immunizations in typical vaccination procedures such as are reported in Klipstein, F. A., et al., 1981. Protective effect of immunization of rats with the holotoxin or B subunit of *Escherichia coil* heat-labile enterotoxin. Infect. Immun. 31:144–150 which is hereby incorporated by reference. The composition of this invention is effective in mammals including humans.

DETAILED DESCRIPTION OF THE INVENTION NH

Figure 1:
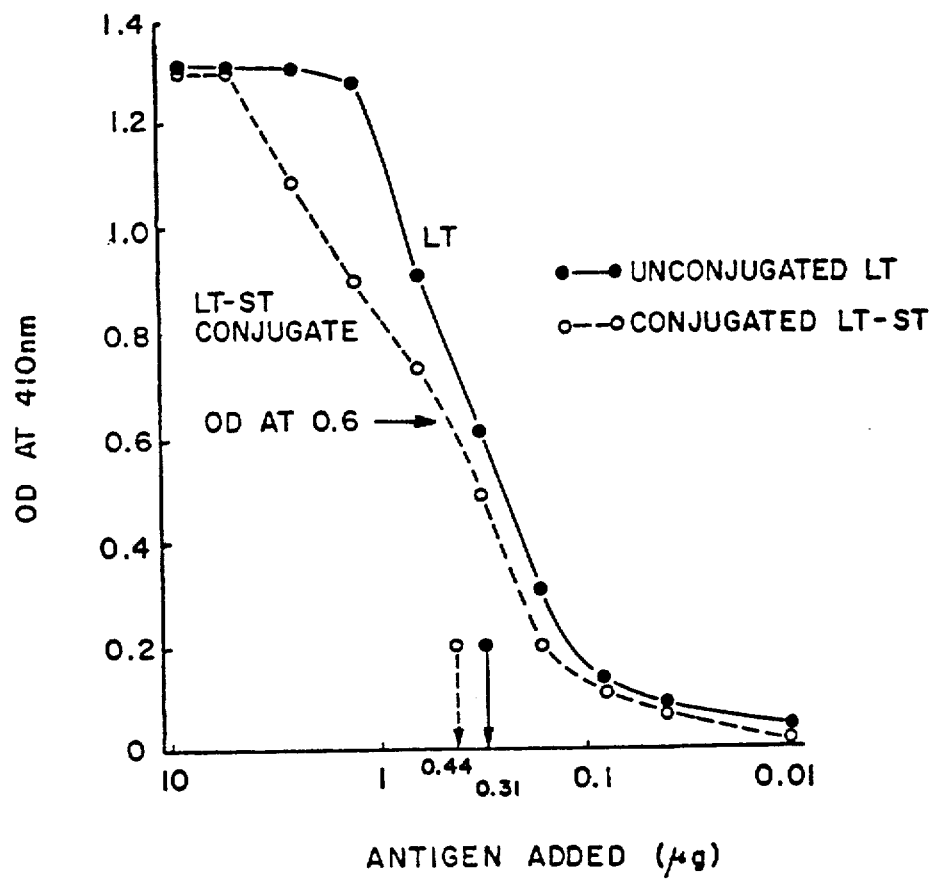
FIG. 1 is a graphical representation of the data obtained and methodology where an enzyme-linked immunosorbent assay (ELISA) was used to compare the antigenicity of different immunogens. Illustrated by a comparison of the LT antigenicity of a preparation of cross-linked ST-LT with LT alone.

The development of a vaccine protocol using the ST and LT or CT (or their B subunit) toxins required that each be manipulated in such a way as to reduce its biological activity and yet continue to be sufficiently immunogenic so as to stimulate an appropriate immune response. Rather than introduce an irrevelant antigen into this equation as a carrier, LT and CT (or their B subunit) were chosen as an immunological vehicle for ST. ST is composed of 10 different amino acids, a total of 18 amino acid residues, one-third of which are half-cystine. Each molecule has three amino groups available for cross-linking to a carrier (two asparagine residues, one of which is the $NH_2$-terminal amino acid) and one carboxyl group available for cross-linking (one glutamic acid residue). LT is composed of 806 amino acid residues (assuming a structural formula $A_1B_5$) with one hundred and thirty three available amino groups (mostly as epsilon amino groups in lysine and arginine) and one hundred forty nine carboxyl groups (present as aspartic acid and glutamic acid). The invention has as its concept to cross-link ST and LT or CT (or their B subunit) via the available carboxyl and amino groups on the two molecules and, additionally, to intrachain link the LT or CT molecules as a means of reducing toxicity.

Water soluble carbodiimides have been used extensively as conjugating reagents in the preparation of conjugated antigens. The most useful water-soluble carbodiimides are 1-ethyl-3-(3-dimethylaminopropyl) carbodiimide (EDAC) and 1-cyclohexyl-3-[2-morpholinyl(4)-ethyl] carbodiimide (MCDI). Any suitable conjugating reagent is useful in the process of the invention to produce cross-linked ST-LT, ST-CT or ST-B. The above mentioned water-soluble carbodiimides are presently preferred.

In the following examples and description of this invention numerous references are made to prior publications. All of these publications are hereby incorporated herein by reference so as to provide a more concise description of this invention.

EXAMPLES

Preparation of the toxins

The LT holotoxin was produced in purified form by the methods described by Clements, J. D. et al., 1979. Isolation and characterization of homogeneous heat-labile enterotoxins with high specific activity from *Escherichia coli* cultures. Infect. Immun. 24:760–769, from *E. coli* strain 711 (F1LT), a transformed K-12 derivative bearing LT gene(s) of the Ent plasmid from porcine strain P307, described by So, M, et al. 1978. Characterization of an *Escherichia coli* plasmid encoding for synthesis of heat-labile toxin: Molecular cloning of the toxin determinant. Infect. Immun. 21:405–411. The homogeneity of this toxin preparation was confirmed by polyacrylamide gel electrophoresis; its biological activity was established by demonstrating its ability to activate Y-1 adrenal cells in tissue culture assay (a standard test for LT activity), and its antigenic homogeneity was confirmed by the demonstration in immunodiffusion of a homogeneous, single band reaction with goat monospecific LT hyperimmune serum. The B subunit was separated from the LT holotoxin by the chromatographic techniques described by Clements, J. D., et al., 1980. Properties of homogeneous heat-labile enterotoxin from *Escherichia coli*Infect. Immun. 29:91–97.

The St toxin was produced from *E. coli* strains 18D (042:H37) and Texas 452 (078:H12), which are $LT^-(ST^+$ strains obtained from human sources, and made in purified form by the method described by Staples, S. J. et al. 1980. Purification and characterization of heat-stable enterotoxin produced by a strain of *E. coli* pathogenic for man. J. Biol. Chem. 255:4716–4721. This process involves the following steps: 1 Culture filtrate →2 Amberlite XAD-2chromatography →3 acetone precipitation →4 first Sephadex G-25 chromatography→5 DEAE Sephacryl chromatography→6 second Sephadex G-25 chromatography→7 thin layer chromatography. The activity of the various products obtained from each processing step was determined by the suckling mouse assay as described by Giannella, R. A., 1976. Suckling mouse model for detection of heat-stable *Escherichia coli* enterotoxin. Characteristics of the model. Infec. Immun. 14:95–99. Values are given in suckling mouse units which are defined as that amount of toxin which yields an intestinal/carcass weight ratio of $\geq 0.083$. Totally pure ST (obtained by step 7) contained 250 mouse units per ug; this material was used for developing specific hyperimmune antisera in rabbits and goats and for the radioiodination studies. Semipure ST, obtained after step 4, contained 185 mouse units per ug; this material was used for the conjugation and immunization studies.

Concentrations of the toxin preparations and their conjugates are expressed in terms of protein content, which was determined by the method of Lowry (See, Lowry, O. H., et al. 1951. Protein measurement with the Folin phenol reagent. J. Biol. Chem. 193:265–275.)Molar equivalents for the toxins were based on published values of 91,450 daltons for the LT holotoxin, 57,400 daltons for the B subunit in their pentamer form, and 2,000 daltons for the ST toxin.

Cross-linking

The LT and ST toxins were cross-linked using the carbodiimide reaction, whose use in general has been reviewed by Bauminger, S. et al. 1980. The use of carbodiimides in the preparation of immunizing conjugates, p. 151-159. In S. P. Colowick and N. O. Kaplan (ed.), Methods in enzymology. Academic Press, New York. Except where specifically noted, the conjugating material was 1-ethyl-3-(3-dimethylaminopropyl) carbodiimide (EDAC). Cross-linked ST-LT compositions were also prepared using 1-cyclohexyl-3-[2-morpholinyl-(4)-ethyl] carbodiimide (MCDI) in order to show that the results of the conjugation procedures were a functiion of cross-linking by a variety of processes rather than being specifically related to EDAC. The details of the cross-linking procedures for each of the different compositions evaluation, and the variable in the cross-linking process (such as ratio of the toxins, sequence of conjugations, amount of EDAC used, pH, temperature and time of the reaction), are described below. In each instance, following completion of the conjugation reaction, the conjugates were exhaustively dialyzed against water using a 12,000 molecular weight cutoff bag which retained the conjugate but not unconjugated ST or the conjugating reagent (i.e., EDAC). The amount of ST present in the final conjugate was indicated by the increased amount of protein over that of the LT or B subunit originally added.

Assay of Toxins and cross-linked LT-ST for toxicity and antigenicity

Each cross-linked ST-LT composition was tested for the properties of ST and LT toxicity and antigenicity, and the results were compared to those obtained by similar tests for the unconjugated toxins. The results are expressed as either the fold change $\Delta$ or the percentage reduction in the cross-linked compositions as compared to the unconjugated toxins.

(a) LT Toxicity was assessed by means of testing serial two-fold dilutions of the test material in tissue culture using Y-1 adrenal cell tissue culture using the methodology described by Sack, D. A. et al. 1975. Test for enterotoxigenic Escherichia coli using Y-1 adrenal cells in miniculture. Infect. Immun. 11:334-336. This assay is a measure of the toxin's ability to stimulate adenylate cyclase and hence, its ability to induce the intestinal mucosa to secrete water and electrolytes.

(b) LT Antigenicity was tested by enzyme-linked immunosorbent assay (ELISA) using published methods (See, Klipstein, F. A. et al. 1981. Protective effect of immunization of rats with the holotoxin or B subunit of Escherichia coli heat-labile enterotoxin. Infect. Immun. 31:144-150). Two-fold serial dilutions of the test material was tested directly against goat hyperimmune serum to purified LT (titer 1:102,000) using rabbit antiserum to goat conjugated with alkaline phosphatase and p-nitrophenyl phosphate as the substrate. The ratio of activity of the conjugate to unconjugated LT was derived from those dosages which yielded an optical density or OD of 600, such as is illustrated in FIG. 1 in which case the antigenicity of the cross-linked LT-ST was reduced 1.4-fold.

(c) ST Toxicity was tested by the suckling mouse assay, as described in Giannella, R. A. 1976 (cited before). Values reported are for the reduction in the mouse units of the cross-linked immunogens as compared to the same amount of unattenuated ST.

(d) ST Antigenicity was evaluated by means of a "double-sandwich" ELISA in which two-fold serial dilutions of the test material were placed between two different hyperimmune sera to ST, which were developed in goats and rabbits to ST; antibody titers of these antisera to ST toxin were 1:131,000. Values for the conjugates were compared to ST in a similar fashion as that described for LT anigenicity.

Rat immunization and challenge

Rats were immunized and challenged using procedures which have been described in detail by Klipstein, F.A. et al. 1981. Protective effect of immunization of rats with the holotoxin or B subunit of Escherichia coli heat-labile enterotoxin. Infect. Immun. 31:144-150. Parenteral immunization was given intraperitoneally using Freund's complete adjuvant for the primary immunization. Peroral (PO) booster immunizations were given via an intragastric tube administered two hours after the peroral administration of cimetidine (available under the trade name Tagamet from Smith, Kline & French Co., Philadelphia, Pa.)to ablate gastric acidity.

Figure 2:
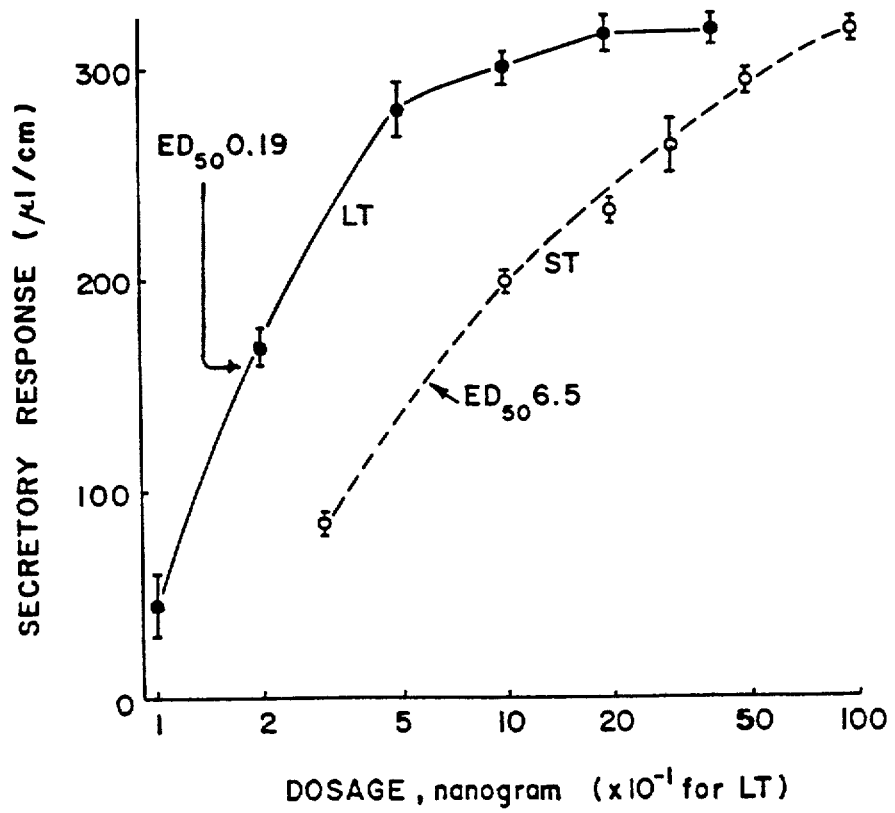
FIG. 2 is a graphical representation of data obtained in determining the secretory response to purified LT and ST in unimmunized rats.

Immunized rats were challenged with the LT and ST toxins and with viable organisms of E. coli strain PB 258, which produces just LT ($LT^{30}/ST^{31}$), strain H 10407 which produces both LT and ST ($LT^{30}/ST^{30}$), and strain Texas 452 which produces just ST ($LT^{31}/ST^{30}$). Each test material was given at that amount which yields maximum secretion in unimmunized animals (as illustrated in FIG. 2). Each datum point was obtained by testing 3 animals. The results are expressed as the mean ± standard error of the mean (SEM) of the percent reduced secretion in immunized rats as compared to the value in unimmunized animals similarly challenged. Reduced secretion of >50% in immunized animals represents a statistically significant ($p<0.001$) difference between the amount of secretion in these rats and in unimmunized control animals.

OBSERVATIONS (1) Factors affecting the cross-linking of ST to LT toxin.

(a) Effect of the ratio of conjugating agent (EDAC) to toxins

Initial studies (the data for which were summarized in Table 2 of the original patent application) indicated that a ratio (by weight) of EDAC to total toxin protein of 45/1 yielded significant cross-linking of ST to LT with reduced LT toxicity (>1000-fold) and ST toxicity (>100-fold) and strong retained antigenicity, whereas an EDAC/toxin ratio of 0.45/1 did not achieve this.

Figure 3:
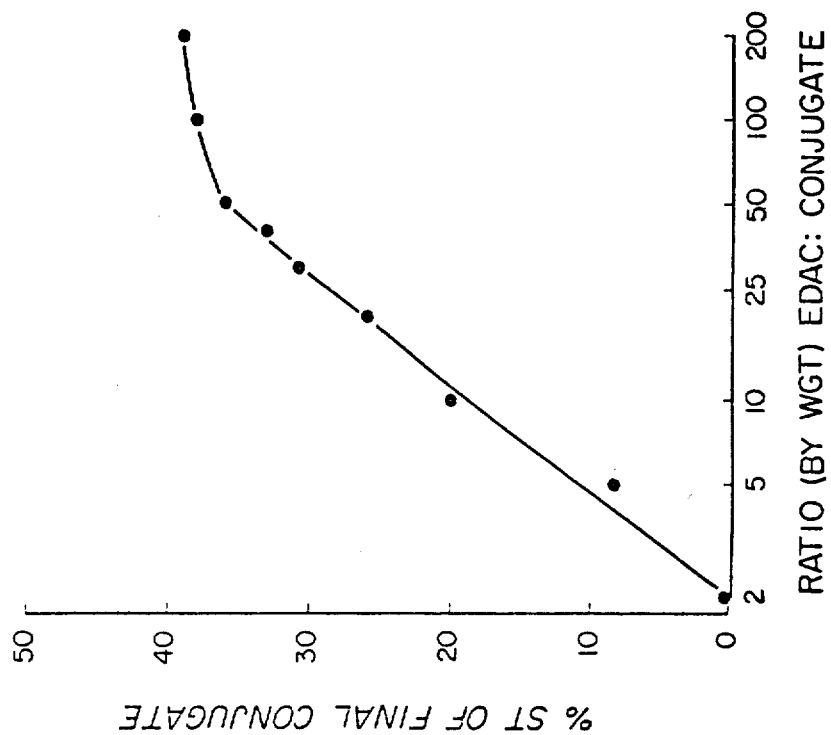
FIG. 3 is a graphical representation of the effect of the ratio of EDAC to total toxin protein or the degree of ST conjugation from a molar ratio of semipure ST/LT of 100/1. Reaction time was 18 hours. Values are the percent ST present in the final conjugate.

In order to determine precisely the optimal ratio of EDAC to toxins necessary to yield the maximum degree of cross-linking, an initial 100/1 molar ratio of ST/LT was exposed to ratios of EDAC to toxin protein that varied between 2/1 and 200/1. The reaction was run at a pH of 7.0, at 20° C., with a reaction time of 18 hours. The results, which are graphically illustrated in FIG. 3, confirm the fact that maximum cross-linking of ST to LT occurs under these conditions at an EDAC/toxin ratio of approximately 45/1.

(b) Effect of the ratio of ST conjugated with LT

Under conditions of conjugation with 100 mg EDAC for a 1 hour exposure time, increasing the initial ST/LT ratio (by weight) resulted in a greater proportion of ST in the final conjugate. The data obtained is presented in Table 1 below.

TABLE 1
EFFECT OF THE RATIO OF ST CONJUGATED WITH LT.

| ST:LT Ratio | Conjugation Process[a] ST mg | LT mg | EDAC mg | Protein Total | Protein % ST | ΔLT Y1 | ΔLT ELISA | ΔST SM | ΔST ELISA |
|---|---|---|---|---|---|---|---|---|---|
| 15:1 | 3 | 0.2 | 100 | 436 | 77 | ND | 1.4 | ND[b] | 3.8 |
| 10:1 | 2 | 0.2 | 100 | 307 | 45 | ND | 1.6 | ND | 3.8 |
| 5:1 | 1 | 0.2 | 100 | 250 | 32 | ND | 1.4 | ND | 14.2 |
| 1:1 | 0.1 | 0.2 | 100 | 227 | 25 | ND | 2.8 | ND | 21.9 |

[a]All reactions were run for 60 min at pH 7.0.
[b]ND signifies not determined.

In order to confirm these observations, pure ST was radioiodinated with carrier free $I^{125}$ by the method of chloramine-T method described by Hunter, R. 1970. Standardization of the chloramine-T method of protein iodination. Proc. Soc. Exp. Biol. Med. Molar ratios of ST/LT or ST/B varying from 1/1 to 200/1 together with a tracer dose of $ST^{125}$ were conjugated at 4° C. for 18 hours in the presence of an EDAC/toxin protein ratio of 45/1.

Figure 4:
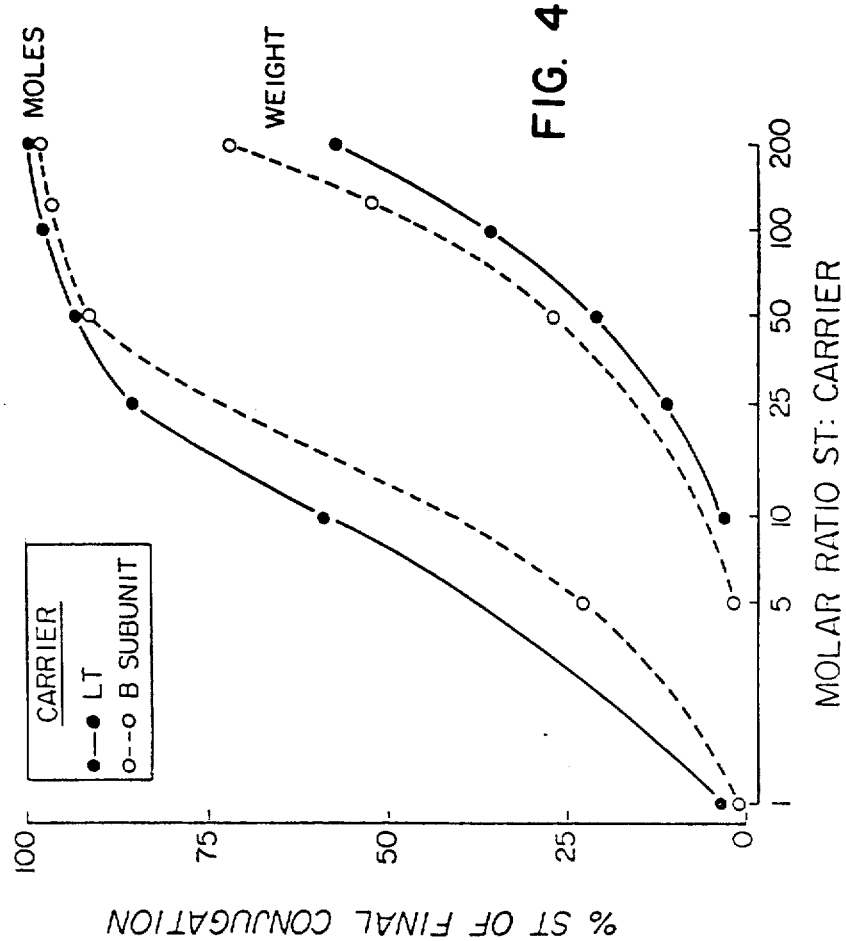
FIG. 4 is a graphical representation of the effect of the initial molar ratio of either pure ST to LT or pure ST to the B subunit on the percentage of ST present in the final conjugate as determined using a tracer dose of radioiodinated ST. The EDAC/total protein ratio was 45/1 and the reaction time was 18 hours.

The results are shown graphically in FIG. 4.

Cross-linked ST-LT

Progressively higher initial ST/LT ratios resulted in a linear increase in the percentage of the ST added to the initial mixture that was retained in the conjugate, thus resulting in progressive increases in the proportion of ST of the final conjugate. Using an initial ST/LT molar ratio of 100/1, the final conjugate contained 96% ST by moles.

Cross-linked ST-B

Progressively higher initial ST/B ratios also resulted in a linear increase in the proportion of ST in the conjugate. Using an initial ST/B molar ratio of 125/1, the final conjugate contained 97% ST by moles.

(c) Effect of duration of the conjugation process

An 18 hour conjugation reaction using an EDAC/toxin protein ratio of 45/1 yielded significantly greater reduction in toxicity of the LT toxin than the 1 hour reaction time. LT and ST antigenicity were not appreciably reduced by the 18 hour reaction in the conjugation sequence of LT+ST+EDAC, but antigenicity was moderately reduced in the other sequences of conjugation. The data obtained is set forth below in Table 2.

TABLE 2
EFFECT OF THE DURATION OF THE CONJUGATION PROCESS

| Conjugation process[a] Sequence | Duration | Protein Total | Protein % ST | ΔLT Y1 | ΔLT ELISA | ΔST SM | ΔST ELISA |
|---|---|---|---|---|---|---|---|
| LT + ST + EDAC | 60 min. | 254 | 24 | 4,333 | 1.6 | >100 | 0 |
| LT + ST + EDAC | 18 hr. | 463 | 59 | 69,333 | 2.1 | >100 | 1.6 |
| LT + EDAC + ST | 60 min. | 263 | 35 | 1,078 | 2.5 | >100 | 0 |
| LT + EDAC + ST | 18 hr. | 363 | 48 | 657,894 | 8.4 | >100 | 8.6 |
| ST + EDAC + LT | 60 min. | 223 | 24 | 267 | 3.5 | >100 | 3.6 |
| ST + EDAC + LT | 18 hr. | 432 | 56 | 17,333 | 6.7 | >100 | 3.2 |

[a]All reactions were with an ST:LT ratio of 10:1 run at pH 7.0, at 20° C. for 60 min. and 4° C. for 18 hr.

Figure 5:
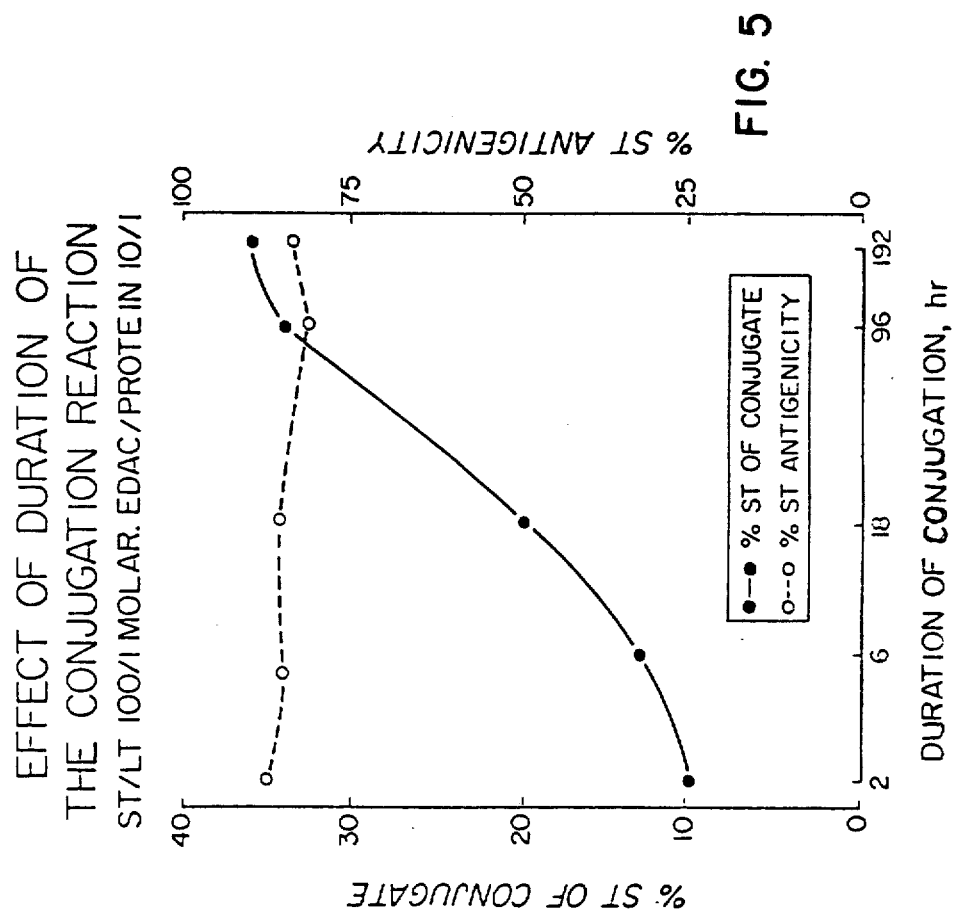
FIG. 5 is a graphical representation of the effect of the duration of the conjugation reaction of the degree of conjugation of semipure ST from an ST/LT molar ratio of 100/1 using an EDAC/total toxin protein ratio of 10/1. Values for antigenicity were derived from corrected samples adjusted to reflect 100% of the toxin.

Additional studies evaluated the effect of varying the conjugation time using a conjugation mixture added in the sequence of LT+ST+EDAC with a molar ratio of ST/LT of 100/1 and an EDAC/toxin protein ratio of 10/1 at pH 7.0 and 4° C. As shown in summary form in FIG. 5, increasing the conjugation reaction time between 2 and 192 hours resulted in a progressive increase in the amount of ST coupled to LT in the absence of significant attenuation of the antigenicity of either conjugated toxin.

(d) Comparison of the effectiveness of different carbodiimides in cross-linking LT and ST Under conditions of conjugation of 18 hours with 100 mg of carbodiimide, both EDAC and MCDI yielded a cross-linked ST-LT molecule which had the characteristics of reduced toxicity with persistent antigenicity. The cross-linked molecule produced with EDAC had appreciably greater reduced toxicity with persistent antigenicity. The data obtained is presented in Table 3 below.

TABLE 3
COMPARISON OF THE EFFECTIVENESS OF DIFFERENT CARBODIIMIDE REAGENTS IN CONJUGATING LT AND ST

| Conjugation[a] Sequence | Protein Total (mg) | Protein ST (%) | ΔLT Y1 | ΔLT ELISA | ΔST SM[b] | ΔST ELISA |
|---|---|---|---|---|---|---|
| LT + ST + EDAC | 463 | 59 | 69,333 | 1.8 | >500 | 1.4 |
| LT + ST + MCDI | 932 | 80 | 10 | 2.6 | >100 | 7.4 |

[a]All reactions used an ST:LT ratio of 10:1 with 100 mg of carbodiimide reagent and were run for 18 hr. at 4° C.
[b]Tested at 500 ng and 2,500 ng.

(e) Conjugation of ST with cholera toxin

E. coli ST may be conjugated with CT holotoxin (or its B subunit) by the same conjugation conditions employed for E. coli ST cross-linking to LT or its B subunit. Conjugation of ST to CT toxin holotoxin or its B subunit follows the same pattern. As pointed out above, the CT toxin is structurally and immunologically similar to the LT toxin. As an example, conjugation of ST to CT using an ST/CT molar ratio of 100/1 and an EDAC/total conjugate ratio of 10/1 for 18 hours yields a conjugate with 54 percent, by weight, and 98 percent, by moles, of ST. The antigenicity of the ST (50 percent) and of CT (51 percent) are maintained in the reaction product.

(2) Optimal cross-linked vaccines and their effectiveness

The previously described observations identified optimum conjugation conditions for cross-linking ST to either LT or its B subunit as an initial molar ratio of 100/1 of ST/LT or ST/B, an EDAC/total toxin protein ratio of 10/1 by weight, and a conjugation reaction time of 96 hours at 4° C.

(a) Cross-linked ST-LT vaccine

The properties of the cross-linked ST-LT immunogen prepared using these conjugation conditions are presented in Table 4 below.

TABLE 4

PROPERTIES OF THE CROSS-LINKED ST-LT VACCINE.

| Toxin | % Wgt | Adjusted to 100%[a] | | Per Unit (ug)[b] | |
|---|---|---|---|---|---|
| | | Toxicity % | Antigenicity % | Toxicity % | Antigenicity % |
| ST | 34 | 0.15 | 82 | 0.06 | 29 |
| LT | 66 | 0.06 | 83 | 0.03 | 51 |

[a]Concentrations of the conjugates were adjusted to reflect 100% of each toxin.
[b]Direct measurements on the uncorrected vaccine.

Immunization

Rats were immunized with this vaccine in dosages of a single 1000 ug intraperitoneal prime and 2500 ug peroral boosts given twice. The total peroral immunization contained approximately 1450 ST antigen units (dosage x antigenicity) and 2550 LT antigen units. As shown in Table 5, this immunization resulted in significant protection against both the LT and ST toxins and viable bacteria which produce these toxins.

TABLE 5

RESULTS OF CHALLENGE IN RATS IMMUNIZED WITH THE CROSS-LINKED ST-LT VACCINE.

| Immunogen used | % Reduced secretion[a] after challenge with[a] | | | | |
|---|---|---|---|---|---|
| | LT toxin | LT+/ST− | LT+/ST+ | ST toxin | LT−/ST+ |
| LT alone | 92 ± 2 | 69 ± 3 | 54 ± 1 | 0 | 3 ± 2 |
| ST-LT | 87 ± 7 | 70 ± 5 | 67 ± 3 | 68 ± 2 | 67 ± 2 |

[a]All values of >50% represent a significant (p < 0.001) reduction in secretion.

(d) Cross-linked ST-B vaccine

The properties of the cross-linked ST-B subunit vaccine prepared using the optimal conjugation conditions listed above under item 2 are shown in Table 6 below.

TABLE 6

PROPERTIES OF THE CROSS-LINKED ST-B VACCINE.

| Toxin | % | Adjusted to 100% | | Per Unit (ug) | |
|---|---|---|---|---|---|
| | | Toxicity | Antigenicity | Toxicity | Antigenicity |
| ST | 30 | 0.14 | 81 | 0.06 | 22 |
| B | 70 | 0.00 | 100[a] | 0.00 | 43[a] |

[a]Determined by ELISA using hyperimmune antiserum to the B subunit.

Immunization

Based on the properties shown in Table 6, the cross-linked ST-B vaccine contained 2,150 B subunit antigen units and 1,100 ST antigen units in a total peroral dosage of 5,000 ug. Immunization of rats with this dosage yielded strong protection against challenge with the viable LT producing strain PB 258 (LT+/ST−) (52±2% reduced secretion) or the viable ST-producing strain Texas 452 (LT−/ST+) (62±1% reduced secretion).

(3) Use of Synthetic ST in the cros-linked vaccine

The novel immunogen of cross-linked ST-LT or ST-B can be created by conjugating ST derived by purification of the toxin from growth of an enterotoxigenic strain of $E.\ coli$ (biologic ST) as described herein or by conjugating synthetic ST produced by an amino acid synthesizer. The sequence of the 18 amino acids which compose purified biologic ST obtained from growing strain 18D (ad described in Staples et al. 1980. Purification and Characterization of heat-stable enterotoxin produced by a strain of $E.\ coli$ pathogenic for man. J. Biol. Chem. 255:4716-4721) has been described by Chan and Giannella, 1981. Amino acid sequence of heat-stable enterotoxin produced by $Escherichia\ coli$ pathogenic for man. J. Biol. Chem. 256:7744-7746. A synthetic ST with this sequence was produced by Dr. Richard Houghten, Scripps Clinic and Research Foundation, La Jolla, California. This synthetic ST toxin has been shown to be biologically and immunologically identical to biologic ST in terms of its ability to evoke fluid secretion in the suckling mouse assay or ligated rat ileal loops and in the capacity of hyperimmune rabbit antiserum to biologic ST to neutralize the secretory effect of either synthetic and biologic ST in the suckling mouse assay.

Synthetic ST was conjugated to the B subunit in reaction which employed and EDAC/total protein ratio of 1.5/1, an ST/B subunit molar ratio of 50/1, and a reaction time of 18 hr. As shown in Table 7, the properties of this vaccine are practically identical to those of the cross-linked biological ST-B vaccine whose properties are summarized in Table 6.

TABLE 7

PROPERTIES OF CROSS-LINKED SYNTHETIC ST-B Subunit VACCINE

| Toxin | % | Adjusted to 100% | | Per Unit (ug) | |
|---|---|---|---|---|---|
| | | Toxicity | Antigenicity | Toxicity | Antigenicity |
| ST | 36 | 0.13 | 85 | 0.06 | 42 |
| B | 64 | 0.00 | 85[a] | 0.00 | 59[a] |

[a]Determined by ELISA using hyperimmune serum to the B subunit.

Immunization of rats with the synthetic ST-B vaccine by the same techniques and at the same dosages described for the biologic ST-B vaccine yielded significant protection against both the LT and ST toxins and viable strains which produce these toxins, as shown in Table 8 below.

TABLE 8

RESULTS OF CHALLENGE IN RATS IMMUNIZED WITH THE CROSS LINKED SYNTHETIC ST-B Subunit VACCINE

| | % Reduced secretion after challenge with[a] | | | | |
|---|---|---|---|---|---|
| LT toxin | LT+/ST− | LT+/ST+ | Synthetic ST | Biologic ST | LT−/ST+ |
| 94 ± 3 | 61 ± 2 | 68 ± 2 | 70 ± 1 | 97 ± 3 | 76 ± 2 |

[a]Values of >50% represent a significant (p < 0.001) reduction of secretion in immunized rats.

These observations show that conjugation of ST toxin, derived either by purification of bacterial growth or produced synthetically, to either LT or CT toxins (either holotoxin or just its B subunit) in the presence of a carbodiimide results in a new molecule, cross-linked ST-LT and ST-CT (or cross-linked ST-B), which has the properties of reduced toxicity and persistent antigenicity for each of the component toxins, and acquired immunogenicity for the ST toxin. EDAC was the most effective conjugating agent but our observations indicate that cross-linking is not specific for this reagent. In vitro studies showed that the following variables influence the cross-linking process: the sequence of conjugation, the concentration of carbodiimide used, the ratio of ST to LT (or its B subunit) used, and the reaction time. The optimum cross-linking reaction yielded a molecule which contained 96% ST by mols, the toxicities of the cross-linked toxins were reduced to ≦0.15% that of the unconjugated toxins while their antigenicities were maintained at >80% as determined by ELISA assay. Similar conjugation conditions also yielded equivalent properties when the ST toxin was cross-linked with the B subunit of the LT enterotoxin or with CT. The immunogenic potency of these molecules was documented by the fact that they provided strong protection in immunized rats against challenge with either the LT or ST toxins themselves or viable bacteria which produce these toxins, either singly or together.

The ratio of ST or LT (or its B subunit) in the conjugate can be varied as can the degree of intramolecular LT holotoxin or B subunit cross-linking by varying the reaction conditions. The ST-LT (or ST-B) conjugate, as such, is unique in that the biological toxicities of both molecules are greatly reduced, the LT (or its B subunit) retains its antigenicity, and ST has aquired immunogenicity as a function of the reaction.

In use, the novel immunogen of this invention can be administered to subjects, animal or human, in a variety of ways. Exemplary methods include parenteral (subcutaneous) administration given with a nontoxic adjuvant such as an alum precipitate or peroral administration given after reduction or ablation of gastric activity, or in a pharmaceutical form that protects the immunogen against inactivation by gastric juice (e.g., a protective capsule or microsphere).

The above results provide evidence that treatment of humans will be accomplished by administering effective amounts of the novel cross-linked ST-LT (or ST-B) composition of this invention.

Another aspect of this invention is the discovery that the heat-labile enterotoxin (either the holotoxin or its B subunit) of either *Escherichia coli* or *Vibrio cholerae* may be employed as a carrier in place of the usual large molecular weight protein. Thus, in accordance with this invention there is provided a novel carrier to which toxins of relatively lower molecular weight can be cross-linked. The LT or CT portion (or its B subunit) of the novel cross-linked product is both a carrier and an immunogen. Both toxins, as indicated above, have greatly reduced toxicity in the combined form yet both act as immunogens. The presence of the B subunit (either as the subunit alone or as part of the holotoxin) enhances the value of this immunogen as a peroral vaccine by virtue of the property of the B subunit to adhere to specific $GM_1$ receptors on the surface of the intestinal mucosa thus rendering close, persistent contact between the immunogen and the mucosa. Although this property of the B subunit (either alone or as part of the LT or CT holotoxin) which enhances peroral immunization has been described as part of the novel cross-linked product of ST-LT or ST-B (in which instance B serves as both a carrier and an immunogen), this unique property of the B subunit of either LT or cholera toxin can be employed when it is used exclusively as a carrier for immunogens other than ST to enhance their effectiveness when given as a peroral vaccine.

Although the invention has been described with respect to specific examples of reagents, adjuvants and conditions, other equivalent compositions and conditions can be utilized without departing from the scope of this invention. The invention has been described largely with respect to specific examples of providing a novel immunogen by cross-linking the ST toxin to the *E. coli* LT holotoxin or its B subunit. The structural, functional and immunological close similarities between the cholera toxin holotoxin and its B subunit and the *E. coli* LT holotoxin and its B subunit make it evident that a similar novel immunogen with the properties described herein is created by cross-linking the *E. coli* ST toxin to either the cholera toxin holotoxin or its B subunit.

We claim:

1. A composition for immunization of mammals against diarrheal disease comprising the product provided by the process which comprises reacting heat-stable (ST) enterotoxin of *Escherichia coli* with a reactant selected from the group consisting of heat-labile (LT) enterotoxin of *Escherichia coli*, the B subunit of said heat labile (LT) enterotoxin, cholera toxin (CT) holotoxin of *Vibrio cholerae*, and the B subunit of said cholera toxin (CT) holotoxin at a molar ratio of ST to reactant of at least 1 to 1 in the presence of a conjugating reagent.

2. The composition of claim 1 in combination with a suitable adjuvant to provide an effective, nontoxic immunogen for use in immunization to protect against diarrheal disease caused by strains of homologous and heterologous somatic serotypes of *Escherichia coli* which produce the heat-labile or heat-stable enterotoxins, either singly or together.

3. The composition of claim 1 wherein the molar ratio of ST to reactant in the reaction mixture is at least 5 to 1.

4. The composition of claim 1 wherein the conjugating reagent is a water-soluble carbodiimide or other effective conjugation reagent.

5. The composition of claim 4 wherein the carbodiimide is 1-ethyl-3-(3-dimethylaminopropyl) carbodiimide.

6. The composition of claim 1 wherein the reaction is allowed to proceed for a period of time in excess of 1 hour.

7. The composition of claim 1 in combination with a suitable adjuvant to provide an effective immunogen for immunological protection against diarrheal disease due to strains of enterotoxigenic *Escherichia coli*.

8. The composition of claim 7 wherein the adjuvant is Freund's complete adjuvant or other suitable adjuvants such as alum.

9. The composition of claim 1 wherein the reactant is the heat-labile (LT) enterotoxin.

10. The composition of claim 1 wherein the reactant is the B subunit of heat-labile (LT) enterotoxin.

11. The composition of claim 1 wherein the reactant is cholera toxin (CT) holotoxin.

12. The composition of claim 1 wherein the reactant is the B subunit of cholera toxin (CT) holotoxin.

13. A method of immunization of mammals against diarrheal disease due to strains of enterotoxigenic *Escherichia coli* which comprises administering an effective amount of the composition of claim 1.

14. The method of claim 13 wherein the composition is administered parenterally.

15. The method of claim 13 wherein the composition is administered perorally.

16. The method of claim 13 wherein the reactant is the heat-labile (LT) enterotoxin or its B subunit.

17. The method of claim 13 wherein the reactant is cholera toxin (CT) holotoxin or its B subunit.

18. The method of claim 13 wherein the mammal is human.

* * * * *